United States Patent [19]

Wojciechowicz

[11] Patent Number: 5,520,685
[45] Date of Patent: May 28, 1996

[54] THERMALLY-INSULATED ANTI-CLOG TIP FOR ELECTROCAUTERY SUCTION TUBES

[75] Inventor: Alex Wojciechowicz, Farmingdale, N.J.

[73] Assignee: Alto Development Corporation, Farmingdale, N.J.

[21] Appl. No.: 285,792

[22] Filed: Aug. 4, 1994

[51] Int. Cl.$^6$ ............................................. A61B 17/39
[52] U.S. Cl. ............................................. 606/49; 604/35
[58] Field of Search ............................... 606/41, 42, 45, 606/49; 604/35

[56] References Cited

U.S. PATENT DOCUMENTS

| | | |
|---|---|---|
| Re. 33,925 | 5/1992 | Bales . |
| 3,828,780 | 8/1974 | Morrison, Jr. ............... 606/49 |
| 3,902,494 | 9/1975 | Haberler . |
| 4,347,842 | 9/1982 | Beale . |
| 4,682,596 | 7/1987 | Bales . |
| 4,932,952 | 6/1990 | Wojciechowicz . |
| 5,277,696 | 1/1994 | Hagen . |

Primary Examiner—Lee S. Cohen
Attorney, Agent, or Firm—Richard C. Woodbridge

[57] ABSTRACT

A suction coagulator includes an improved anti-clog tip. The anti-clog tip is located at the distal end of a hollow, conductive tube, the proximal end of which is connected to a handle. An interior channel runs through the conductive tube and the handle through a suction fitting thereon to a conventional source of suction. The handle also includes an electrical connection for providing electrical power to the conductive tube. An insulating layer surrounds the exterior sidewall of the conductive tube and is stripped back a distance $D_O$ of 0.050 to 0.200 inches from the distal end of the conductive tube. A thermal insulating sleeve or coating is located inside of the interior channel of the conductive tube and extends from the distal end a distance $D_I$ into said interior channel. The distance $D_I$ is approximately 1½ to 3 times the outside diameter $OD_C$ of the conductive cannula tube. The insulating sleeve provides substantial thermal insulation and some electrical insulation. In a preferred embodiment of the invention, the distal end of the tube is flared into a bell creating an air gap having a width of $D_G$ between the insulation sleeve and the inside diameter $ID_B$ of the bell. The outside diameter of the bell is approximately equal to the outside diameter $OD_C$ of the hollow, conductive cannula tube.

17 Claims, 3 Drawing Sheets

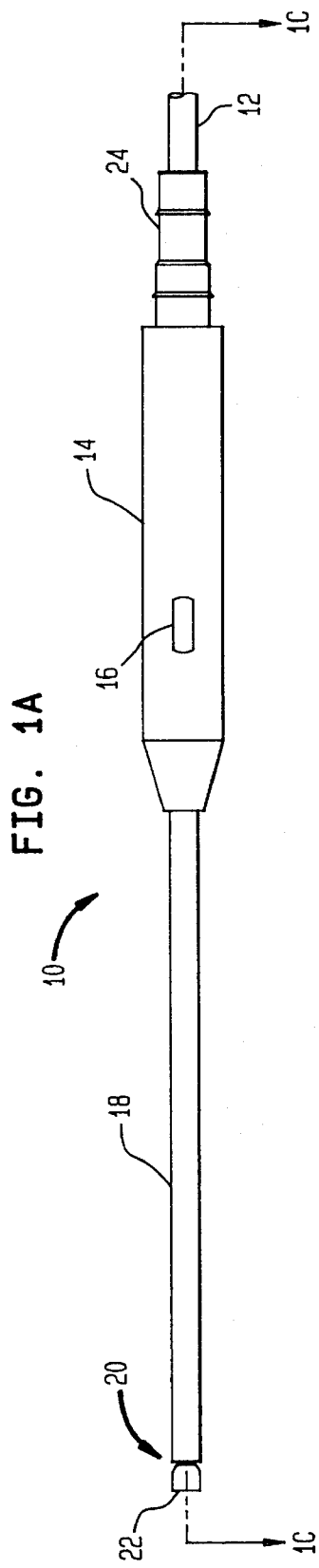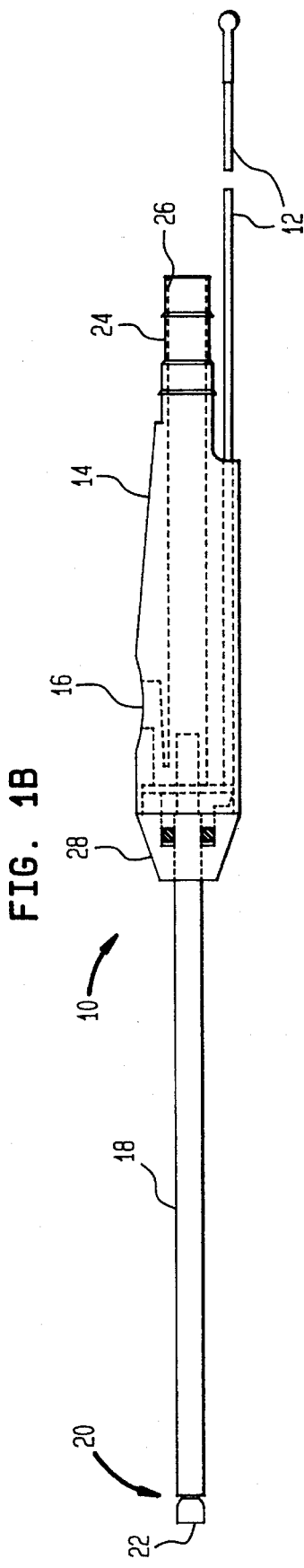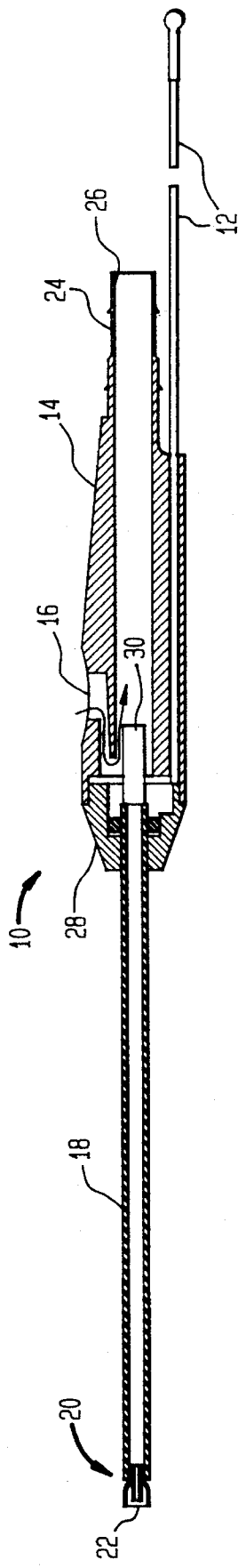

5,520,685

THERMALLY-INSULATED ANTI-CLOG TIP FOR ELECTROCAUTERY SUCTION TUBES

BACKGROUND OF THE INVENTION

1. Field of the Invention

The invention relates to a suction electrocoagulator apparatus having an anti-clogging tip which includes a thermally insulating sleeve that extends from the distal end of the hollow, conductive cannula tube into the interior cavity of said tube.

2. Description of Related Art

The coagulation of bleeding blood vessels using electrically conductive suction tubes, also referred to as cannulas, is a technique widely used for over two decades. A combined electrocautery and suction tube instrument is typically employed in surgery wherever excessive blood must be removed from the bleeding site in order to facilitate hemostat of bleeding vessels using the electrocautery feature of the instrument.

Commercially available suction coagulators made expressly for electrocautery hemostat procedures generally have the following common components:

(A) A hollow, metallic, conductive cannula tube having a suitable thickness of non-conducting electrical insulation on its exterior. The electrical insulation is absent from the first few millimeters on the tube's distal end in order to form an annular ring for electrocautery procedures. The sole purpose of the insulation is to protect the patient and doctor from cautery burns that would result from contact with the outside of the metallic tube when it is energized.

(B) A non-metallic or electrically insulated handle. The handle includes a suction cavity or passageway running through its length that terminates in a suction fitting at one end for connection to a suction source. At its proximal end the handle is hermetically coupled to the hollow, metallic tube so that the suction cavity of the handle communicates directly with the suction channel of the tube. The handle may also have a venting passageway that connects the main suction cavity with a vent hole on the handle's exterior. The surgeon uses finger pressure on the vent hole to control the amount of suction applied.

(C) A power cord, typically in an insulated wire, is used to connect the suction coagulator to a high frequency current generator. The power cord enters the handle and is electrically connected to the proximal end of the conductive suction tube using various known connecting techniques.

One of the major problems with electrocautery suction devices is that the tips tend to clog with burned tissue and coagulated blood. In theory, the suction is supposed to remove the clog but the suction itself produces some problems.

One approach has been to control the flow of air through the suction tip by means of a vent hole that can be manipulated by the surgeon. A useful description of the prior art problems is found in my prior U.S. Pat. No. 4,932,952 entitled ANTISHOCK, ANTICLOG SUCTION COAGULATOR. The following patents were cited as being relevant to that approach: U.S. Pat. Nos. 2,888,928; 3,595,234; 3,610,242; 3,828,780; 3,857,945; 3,974,833; 4,427,006; 4,562,838; and 4,719,914.

Another approach to minimize the coagulating of tissue in an electrocautery suction instrument is described in U.S. Pat. No. 3,902,494 entitled SUCTION SURGICAL INSTRUMENT. The general concept described therein provides for an electrode at the tip of the instrument located in such a way as to impede the introduction of tissue mass into the tube. By restricting the size of the opening with the conducting electrode, it is possible to filter out tissue that otherwise might clog the instrument downstream. One embodiment described in the text of U.S. Pat. No. 3,902,494, but not illustrated in its drawings, comprehends an electrical lead shaped as a tube which encompasses the suction shaft 10. The purpose appears to be to increase the stiffness of the suction shaft. In that embodiment, it is assumed that the electrode tip of the suction device is likewise restricted to prevent tissue clogging as taught by the other illustrated embodiments of the invention. Insofar as understood, U.S. Pat. No. 3,902,494 is directed at the concept of preventing tissue clogging and does not appear to address the more difficult issue of clogging caused by the coagulation of blood at the mouth of the cannula due to the heat generated by the electrocautery effect.

U.S. Pat. No. 4,682,596 entitled MEDICAL HIGH FREQUENCY COAGULATION INSTRUMENT describes a specialized structure incorporating an insulating hose inside of a ring electrode which is part of a much more complicated overall structure involving a second ring electrode and an exterior insulating layer as well as an intermediate insulating layer. The purpose of the device appears to provide a supply of "flushing liquid" which emerges around the interior electrode and then is sucked down through the central shaft of the interior electrode.

U.S. Pat. No. 4,682,596 and its counterpart U.S. Pat. No. Re. 22,925 both describe a catheter employing an electrode and an electrically insulating tube. In that embodiment, the electrode appears to cover the entire front face of the device as illustrated in FIGS. 3 and 4 thereof. There is a discussion in column 8, lines 44–47 that addresses the insulating properties of the support for the electrode tip.

Lastly, U.S. Pat. No. 4,347,842 entitled DISPOSABLE ELECTRICAL SURGICAL SUCTION TUBE AND INSTRUMENT is cited as being of general possible relevance only.

While the prior art selectively discloses the concept of restricting tissue from entering the tip of an electrocautery tube so as to prevent clogging of the tube, nevertheless, it does not appear to appreciate the problem of blood coagulation at the tip due to electrocautery heating. Accordingly, none of the prior art located and described above appears to fully appreciate the necessity of providing appropriate thermal insulation at the tip in order to avoid blood coagulation. The invention described in detail later in this specification, provides a dramatic improvement over prior art devices such as described above by virtue of the fact that it substantially eliminates the problem previously associated with the formation of eschar, i.e. blood char, in the tip of electrocautery suction devices.

SUMMARY OF THE INVENTION

Briefly described, the invention comprises a suction electrocoagulator apparatus having an improved anti-clog tip. The anti-clog tip is located at the distal end of a hollow, conductive, cannula tube. The cannula tube includes an exterior sidewall, the distal end, a proximal end at the opposite end of the tube from the distal end, and an interior channel for connecting the proximal and distal ends together. The proximal end of the conductive tube is connected to the front end of a handle. A suction fitting is located on the rear end of the handle and is employed to communicate the interior cavity of the conductive tube to a source of suction. The handle also includes an electrical connector for providing high-frequency current to the tip of the conductive tube. Electrical insulation, in the form of a coating or sleeve, surrounds the exterior of the conductive tube and is stripped back by approximately 0.050 to 0.200 inches from the distal end of the conductive tube.

The improvement comprises a thermal insulating sleeve located inside of the interior channel of the conductive tube and extending a distance $D_I$ into the interior channel. The distance $D_I$ is preferably in the range of one and one-half to three times the outside diameter of the hollow, conductive, cannula tube. The insulating sleeve preferably provides both electrical and thermal insulation. The insulation can comprise either a combined sleeve or two discrete sleeves, one for thermal insulation and one for electrical insulation, located concentrically within each other.

An alternative embodiment of the invention calls for flaring the distal end of the electrically conductive, hollow, metallic, cannula tube into a bell, the outside diameter $OD_B$ of which is larger than the outside diameter $OD_I$ of the cannula tube and the inside diameter which is larger than the downstream inside diameter $ID_C$ of the conductive tube. An insulator providing both electrical and thermal insulation is located on the inside of the bell and includes a channel therethrough that has a diameter $ID_S$ that is approximately the same as the inside diameter $ID_C$ of the conductive tube.

The preferred embodiment of the invention calls for flaring the tip of the hollow, metallic, conductive cannula tube into a bell having an outside diameter $OD_B$ approximately equal to the outside diameter $OD_I$ of the insulating coating on the outside of the conductive tube. A cylindrical, insulating sleeve is inserted into the distal end of the anti-clog tip so that it extends a small distance $D_S$ beyond the bell and a distance $D_I$ into the throat of the anti-clog tip. An annular gap having a width $D_G$ is formed between the outside surface of the cylindrical insulating sleeve and the inside surface of the bell. The air gap between the insulating sleeve and the inside surface of the bell provides additional thermal insulation. Even though the cylindrical insulating sleeve slightly restricts the inside diameter of the cannula tube, nevertheless, the results are significantly improved because of the additional thermal insulating provided by the air gap between the insulating sleeve and the inside surface of the bell.

These and other features of the present invention will be more fully understood by reference to the following drawings.

BRIEF DESCRIPTION OF THE DRAWINGS

FIG. 1A is a top plan view of the invention including the anti-clog tip.

FIG. 1B is a side elevation view of the embodiment of FIG. 1A.

FIG. 1C is a side cross-sectional view of the embodiment of FIGS. 1A and 1B.

DETAILED DESCRIPTION OF THE INVENTION

Figure 2:
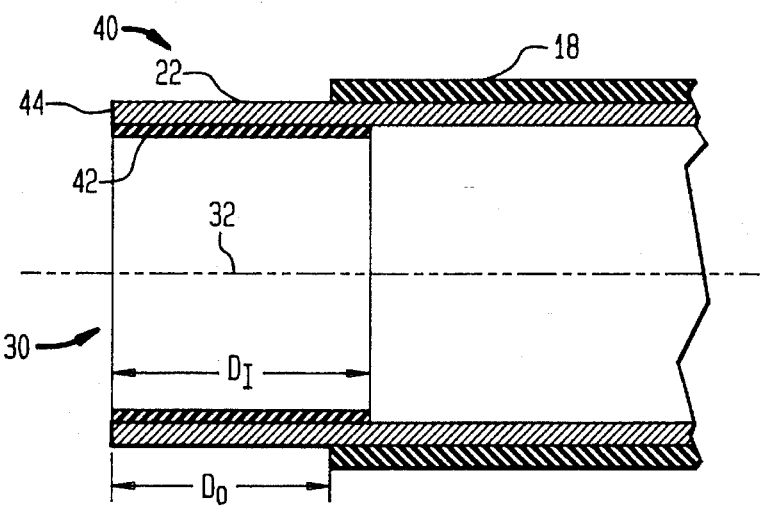
FIG. 2 is a side, cross-sectional view of an early, but relatively ineffective, prototype of the present invention illustrating a thin polytetrafluoroethylene coating extending from the distal end of the tip into the interior channel of the conductive cannula tube.

During the course of this description like numbers will be used to identify like elements according to the different figures which illustrate the invention.

FIGS. 1A, 1B and 1C, illustrate different views of the present invention 10 in which the improved, anti-clog tip 20 is shown in its normal context. The invention 10 typically includes an electrical conductor 12, which is connectable to a conventional source of high frequency current, a handle 14, a vent hole 16, and cannula tube 22. Cannula tube 22 is surrounded by an electrically insulating coating 18 which is stripped back a distance of $D_S$ from the distal end of the hollow, conductive, metallic cannula tube 22. The proximal end of the cannula tube 22 is connected to the front end 28 of handle 14. A suction fitting 24 is located at the rear of handle 14 and connects with a hollow interior cavity 26 which communicates with the interior cavity and opening 30 of the cannula 22. Handle structures that might be suitable for use with the present invention 10 are described in the prior art. See, for example, U.S. Pat. No. 3,828,780 and my U.S. Pat. No. 4,932,952 previously discussed.

FIGS. 2–6 illustrate various different embodiments of the improved anti-clog tip 20 in further detail.

According to FIG. 2, the electrically conductive, tubular cannula 22 extends a distance $D_O$ beyond the exterior insulating sleeve 18. Conductive tube 22 has a central axis 32 and a front opening 30 which draws in air and blood under the influence of suction applied to suction fitting 36 as illustrated in FIGS. 1A–1C. The embodiment 40, of FIG. 2, includes a front face 44 and a thin interior Teflon® sleeve 42 which extends a distance $D_I$ from the front face 44 into the interior of the electrically conductive tube 22. The purpose of sleeve 42 was to provide electrical insulation but not thermal insulation. The distance $D_I$ extended approximately 1½ to 3 times the diameter of the tube into the suction channel. For tonsillectomy procedures the interior diameter of the tube is typically 0.100 inches, and the outside diameter of the tube 22 is typically 0.120 inches and, therefore, the distance $D_I$ might vary between 0.150 to 0.360 inches. While the electrical insulation embodiment 40 of FIG. 2 works (with proper sizing of the Teflon® sleeve thickness), it does not provide the dramatically improved level of results achieved with embodiments 3–6, described below.

Figure 3:
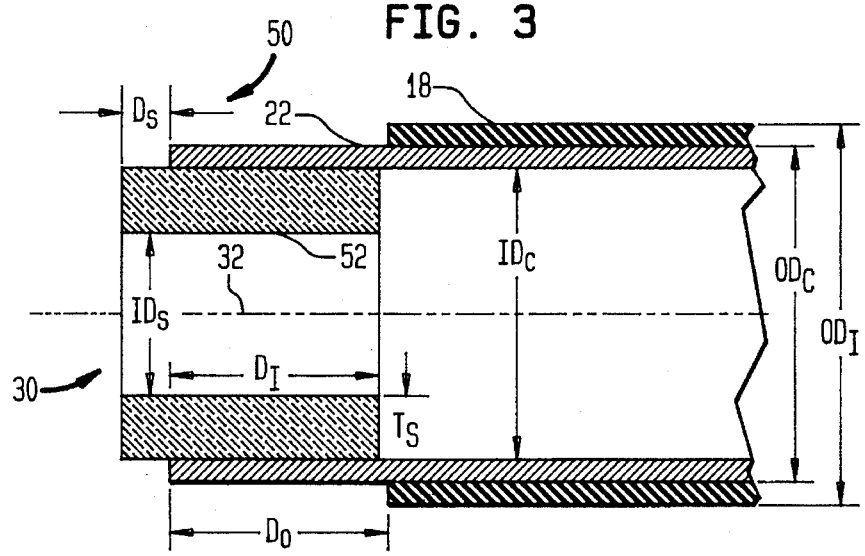
FIG. 3 illustrates an improved embodiment of the present invention including a combined or integrated electrical and thermal insulating sleeve that extends a distance $D_S$ beyond the distal end of the conductive cannula tube and a distance $D_I$ into the throat of the cannula tube.

Embodiment 50, illustrated in FIG. 3, includes a tubular electrode 22, which extends a distance $D_O$ beyond the outer electrical sleeve 18. An electrical and thermal insulating sleeve or coating 52 is located within the inside diameter of cannula 22 and extends a distance $D_S$ beyond the front face 44 of cannula 22. The distance $D_S$ should be short enough so that the electrical and thermal insulating sleeve 52 does not interfere with the surgeon's ability to touch tissue with the cautery tip face 44. The minimum distance $D_I$ that the sleeve 52 must extend into the cannula 22 may be derived empirically but testing indicates that a distance of 1½ to 3 times the outside diameter of the cannula tube 22 is adequate (i.e., $D_O=1½-3$ $OD_C$). The thickness $T_S$ of the sleeve 52 depends upon the physical properties of the thermal insulating material selected. It must be thick enough to prevent the passage of most of the heat of cautery while at the same time insulating the inside surface from most or all of the electrocautery current. The design parameters for this are complex. The material of the sleeve 52 must be biocompatible, have low thermal conductivity, high electrical resistivity, and be capable of withstanding temperatures up to approximately 500° F. Good candidate materials for sleeve 52 would include, but not be limited to, glass, or high temperature plastics such as Teflon® (polytetrafluoroethylene), polysulfone, polyethersulfone, or polyetherimide. The preferred electrical resistivity of the sleeve is greater than $10^{12}$ ohm cm and preferably about $10^{16}$ ohm cm. For good results the material selected should have a thermal conductivity less than 0.6 $^{BTU}/_{hrft° F}$. While the foregoing thermal conductivity is good, the apparatus also operates satisfactory with a sleeve thermal conductivity of approximately 0.10 $^{BTU}/_{hrft° F}$.

According to the preferred embodiment, the cannula tube 22 is preferably made from an electrically conducting material such as brass, aluminum or steel. The basic electrical insulation 18 on the outside of the cannula 22 is preferably polyolefin but could be PVC, PTFE or any other flexible, suitable plastic material. The insulation 18 is preferably stripped back a distance $D_O$ of 0.05 to 0.200 inches from the bare cautery tip face 44 of the cannula 22.

Figure 4:
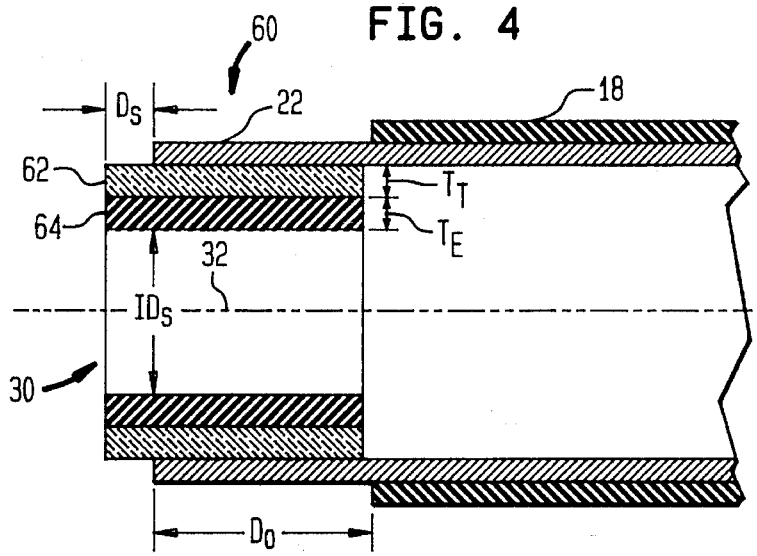
FIG. 4 illustrates another embodiment of the present invention employing separate electrical and thermal insulating sleeves, concentrically positioned, as opposed to the integrated sleeve illustrated in FIG. 3.

FIG. 4 illustrates an embodiment 60 in which the insulating sleeve can comprise two concentric sleeves 62 and 64. According to the preferred embodiment, the innermost sleeve 64 comprises an electrical insulating material preferably PTFE, FEP, PFA, or polyetherimide. Its thickness $T_E$ is preferably 0.010 and in the range of 0.003 to 0.020 inches. Thermal insulating sleeve 62 surrounds the electrical insulating sleeve 64 and has a thickness $T_T$ of approximately 0.010 and could be in the range of 0.005 to 0.020 inches. The preferable material for the thermal insulating sleeve 62 is filled epoxy but could be filled silicone or fiberboard.

Figure 5:
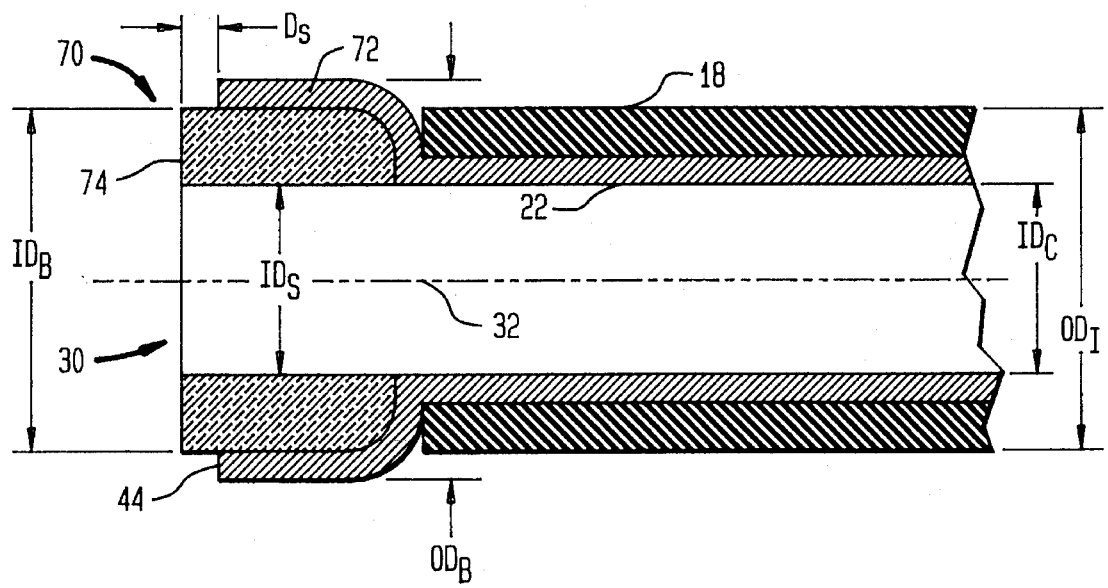
FIG. 5 illustrates another embodiment of the present invention in which the conductive, cannula tube is flared into a bell at its distal end and in which the insulating sleeve is positioned within the bell such that the inside diameter of the apparatus from the bell section through the conductive tube remains essentially unchanged.

An improved alternative embodiment 70 is illustrated in FIG. 5. Embodiment 70 includes a modified tip that preserves the inside diameter $ID_C$ while utilizing the basic design principles of the present invention to prevent blood coagulation due to thermal heating. According to embodiment 70, the end of the conductive cannula tube 22 is flared to form a bell 72. The outside diameter $OD_B$ of the bell 72 is larger than the outside diameter $OD_I$ of the insulating sleeve 18. It is possible with this structure to place an electrical and thermal insulating sleeve 74 into the mouth of the bell 72 in such a way that the inside diameter $ID_S$ of the sleeve 74 is approximately the same or greater than the downstream inside diameter $ID_C$ of the conductive cannula tube 22. According to the tip embodiment 70, the sleeve 74 could be a homogenous material having both electrical and thermal insulating properties, such as illustrated by sleeve 52 in the embodiment 50 illustrated in FIG. 3. Alternatively, the sleeve 74 could be comprised of two separate concentric sleeves, one for thermal insulation and the other for electrical insulation, such as sleeves 62 and 64 illustrated in embodiment 60 of FIG. 4. This embodiment, however, requires an awkwardly large outside diameter of the bell in order to accommodate sufficient thickness for the electrical and thermal insulating sleeve(s) 74. Another version of embodiment 70 would be to reduce the outside diameter $OD_B$ of the bell while making the insulating sleeve inside diameter $ID_S$ somewhat less than the downstream inside diameter $ID_C$ of the conductive cannula.

Figure 6:
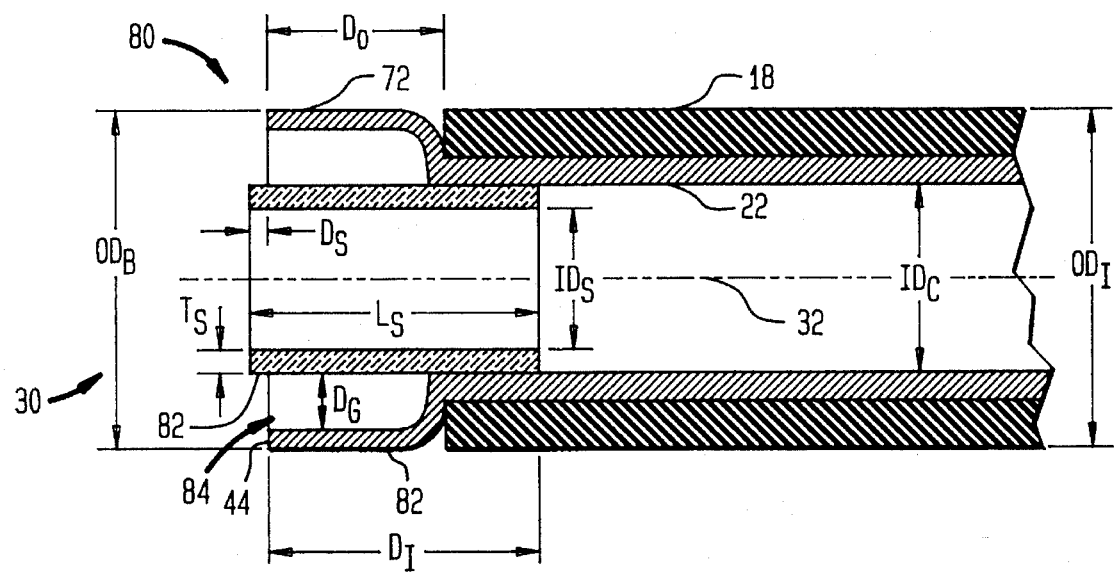
FIG. 6 is a cross-sectional view of the preferred embodiment of the invention in which the conductive tube is flared into a bell at its distal end as in FIG. 5 and in which an insulating sleeve is located within the throat of the tip creating a thermally insulating air gap between the exterior surface of the cylindrical insulating sleeve and the interior surface of the bell.

The preferred tip embodiment 80 of the invention 10 is illustrated in FIG. 6. This tip was the most successful of those used in field trials. It was especially useful for the type of electrocautery suction tubes that are used in tonsillectomy, adenoidectomy, or sinuscopy procedures. According to the preferred embodiment 80, it is desired to use a bell-shaped tip 72, such as illustrated by embodiment 70 of FIG. 5, but, because of surgeon's preference, to limit the outside diameter of the bell $OD_B$ to approximately match the outside diameter $OD_I$ of the external insulation 18. An electrical/thermal insulating sleeve 82 having an inside diameter $ID_S$ is located in the opening 30 of the instrument and extends a distance $D_S$ beyond the front face 44 of the bell 72 and has a length $L_S$ sufficient so that it extends into, and is held in place by, the sidewalls of the upstream cannula tube 22. The exterior wall of the insulating sleeve 82 defines an air gap 84 with respect to the interior wall of the flared, bell section 72 of the cannula tube 22. The annular air gap 84 formed between the sleeve 82 and the bell 72 acts as a very good thermal insulator so that the required thickness of the insulating sleeve 82 is largely reduced to the minimum required for electrical insulating properties. While it is possible to fill the gap 84 with a thermal insulator, it is has been found that the air gap 84 provides more than adequate thermal insulation with a sleeve 82 having a thickness $T_S$ of approximately 0.010 inches for tonsillectomy size suction tubes.

EXPERIMENTAL RESULTS

The results achieved by using the basic invention, especially embodiments 70 and 80, illustrated in FIGS. 5 and 6, were exceptionally good. For years electrocautery suction tube designers have attempted to minimize clogging by modifying the port designs such as described in my prior U.S. Pat. No. 4,932,952. While the modified port designs improved the situation, they did not remedy the underlying problem, namely that the tips would still clog. Accordingly, tests were initiated to try to determine the root causes for tip clogging.

It was generally thought, prior to the time of the present invention, that the cause of rapid coagulation of blood within the tip of electrocautery suction tubes was the direct result of the fulguration effects of the electrocautery current discharged at that location. Therefore, my first approach was to attempt to electrically insulate the inside diameter and tip end with a 0.006 inch coating of polytetrafluoroethylene (i.e., Teflon®) as illustrated in embodiment 40 of FIG. 2. The coating 42 extended a distance $D_I$ of approximately ½ inch into the tube 22 from its tip 44 and its thickness essentially precluded the conductance of current in the coated area through resistive or capacitive means. The concept was to drive all the cautery current to the outside of the tip 40. Embodiment 40 was tested at the North Carolina State University College of Veterinary Medicine using fresh drawn horse blood. Suction tubes having tips with and without the coating 42 were each placed into a 100 ml plastic cup filled with horse blood. The ESU generator was set at 50% coagulation power and activated with moderate suction applied to the suction port. Without exception, the uncoated samples clogged within 10 to 20 seconds and the coated ones did not. Moreover, the inside diameters of the coated samples were completely clean.

Initially, it was believed that embodiment 40, illustrated in FIG. 2, solved the problem, but it was later discovered through actual use in tonsillectomy procedures that those tubes clogged almost as often as the uncoated ones.

It was then observed that the laboratory tests did not simulate actual use of the device in one important aspect, namely, that in the laboratory the tip of the cannula was always submerged in blood that was being drawn up into the cannula. The circulating blood kept the tip cool by removing the heat generated by cautery. In actual use, however, suction is used first to remove most of the blood to visualize the bleeder area so that when cautery is applied only a mixture of air and a small amount of blood passes up the cannula to cool the tip. Therefore, the laboratory protocol provided much more liquid cooling of the cautery tip than was found in actual use. This observation led correctly to the speculation that the coagulation of blood within the cautery tip could be minimized if the cautery tip was insulated inside the diameter from both the electrocautery current and the heat it generated. The resulting tip is a structure that easily and economically prevents the clogging of electrocautery tips from both tissue and blood in a safe, dependable manner.

While the invention has been described with reference to a preferred embodiment, it will be appreciated by those of ordinary skill in the art that modifications can be made to the structure and function of the basic invention without departing from the spirit and scope of the invention as a whole.

I claim:

1. A suction coagulator apparatus having an improved anti-clog tip, said apparatus comprising:

a hollow, conductive tube having an exterior sidewall, a distal end, a proximal end at the opposite end of said tube from said distal end, and an interior channel therethrough for connecting said proximal and distal ends;

a handle having a front end attached to the proximal end of said tube, a rear end having a suction fitting thereon, and an interior cavity for connecting said suction fitting to the interior channel in said tube such that when suction is applied to said suction fitting, air is drawn through the distal end of said tube in a downstream direction through the channel in said tube and then through said interior cavity to said suction fitting;

electrical connection means attached to said handle for making electrical connection with said tube;

an insulation coating surrounding the exterior sidewall of said conductive tube and stripped back a distance $D_O$ from the distal end of said tube; and, insulating means located inside of said interior channel of said conductive tube and extending from said distal end a distance $D_I$ into said interior channel, wherein said insulating means prevents clogging of blood inside of the distal end of said tube.

2. The apparatus of claim 1 wherein said insulating means comprises an electrical insulation sleeve.

3. The apparatus of claim 2 wherein the electrical resistivity of said sleeve is greater than $10^{12}$ ohm cm.

4. The apparatus of claim 3 wherein the electrical resistivity of said sleeve is approximately $1 \times 10^{16}$ ohm cm.

5. The apparatus of claim 1 wherein said insulating means comprises a thermal insulation sleeve.

6. The apparatus of claim 5 wherein the thermal conductivity of said sleeve is less than 0.6 $^{BTU}/_{hrft° F}$.

7. The apparatus of claim 6 wherein the thermal conductivity of said sleeve is approximately 0.10 $^{BTU}/_{hrft° F}$.

8. The apparatus of claim 1 wherein said insulating means comprises an electrical and thermal insulation sleeve.

9. The apparatus of claim 1 wherein said hollow, conductive tube has an outside diameter $OD_C$ and wherein the distance $D_I$ is approximately 1½–3 times $OD_C$.

10. The apparatus of claim 1 wherein the material of said insulating means is taken from the group consisting of: glass, ceramic, or high-temperature plastic selected from the group consisting of polyfluorocarbon, polysulfone, polyethersulfone, polyamide, polyetherimide, silicone, or epoxy.

11. The apparatus of claim 1 wherein said insulation coating surrounding said exterior sidewall of said conductive tube is stripped back from the distal end of said tube by a distance $D_O$ that is approximately in the range of 0.050 to 0.200 inches.

12. The apparatus of claim 1 wherein said conductive tube has a downstream inside diameter $ID_C$ and wherein said distal end of said tube is flared into a bell having an interior surface and an inside diameter $ID_B$ greater than the downstream inside diameter $ID_C$ of said conductive tube.

13. The apparatus of claim 12 further comprising an air gap having a width $D_G$ between said insulating means and said interior surface of said bell.

14. The apparatus of claim 13 wherein said exterior insulation coating has an outside diameter of $OD_I$ and wherein said bell has an outside diameter $OD_B$ which is substantially equal to said outside diameter $OD_I$ of said exterior insulation coating.

15. In a suction coagulator of the type having a hollow, conductive tube, including an exterior sidewall, a distal end, a proximal end at the opposite end of said tube from said distal end, and an interior channel therethrough for connecting said proximal and distal ends, and a handle attached to the proximal end of said conductive tube, said handle including a suction fitting for mating with a source of suction and an electrical connection for providing electrical power to said conductive tube, the improvement comprising:

an insulation coating surrounding the exterior sidewall of said conductive tube and stripped back a distance $D_O$ from the distal end of said tube; and, insulating means located inside of said interior channel of said conductive tube and extending from said distal end a distance $D_I$ into said interior channel, wherein said tip apparatus substantially eliminates the burning of blood and the clogging of the inside of the distal end of said conductive tube by substantially preventing the blood in said tube from heating up and coagulating during electrocautery procedures.

16. The apparatus of claim 15 wherein said conductive tube has a downstream inside diameter of $ID_C$ and wherein said distal end of said tube is flared into a bell having an inside surface and an inside diameter of $ID_B$ greater than said downstream inside diameter $ID_C$ of said conductive tube.

17. The apparatus of claim 16 further comprising an air gap between said insulating means and said inside surface of said bell, said air gap having a width of $D_G$.

* * * * *